(12) United States Patent
Vancelette et al.

(10) Patent No.: US 8,298,221 B2
(45) Date of Patent: Oct. 30, 2012

(54) DISPOSABLE SHEATH WITH REPLACEABLE CONSOLE PROBES FOR CRYOSURGERY

(75) Inventors: David W. Vancelette, San Diego, CA (US); Douglas A. Devens, Jr., Highland Park, IL (US)

(73) Assignee: CooperSurgical, Inc., Trumbull, CT (US)

( * ) Notice: Subject to any disclaimer, the term of this patent is extended or adjusted under 35 U.S.C. 154(b) by 1345 days.

(21) Appl. No.: 11/942,219

(22) Filed: Nov. 19, 2007

(65) Prior Publication Data

US 2008/0119838 A1 May 22, 2008

Related U.S. Application Data

(60) Provisional application No. 60/866,335, filed on Nov. 17, 2006.

(51) Int. Cl.
*A61B 18/18* (2006.01)

(52) U.S. Cl. .......................................................... 606/24

(58) Field of Classification Search ............... 606/20–26
See application file for complete search history.

(56) References Cited

U.S. PATENT DOCUMENTS

| | | | |
|---|---|---|---|
| 3,398,738 A | 8/1968 | Lamb et al. | |
| 3,827,436 A | 8/1974 | Stumpf et al. | |
| 4,211,231 A | 7/1980 | Rzasa | |
| 4,802,475 A | 2/1989 | Weshahy | |
| 5,139,496 A | 8/1992 | Hed | |
| 5,275,595 A | 1/1994 | Dobak, III | |
| 5,281,217 A | 1/1994 | Edwards et al. | |
| 5,324,286 A | 6/1994 | Fowle | |
| 5,400,602 A | 3/1995 | Chang et al. | |
| 5,403,309 A | 4/1995 | Coleman et al. | 606/20 |
| 5,423,807 A | 6/1995 | Milder | |
| 5,573,532 A | 11/1996 | Chang et al. | |
| 5,599,295 A | 2/1997 | Rosen et al. | |
| 5,690,605 A | 11/1997 | Hamlin et al. | |
| 5,716,353 A | 2/1998 | Matsuura et al. | |

(Continued)

FOREIGN PATENT DOCUMENTS

EP 0624347 11/1994

(Continued)

OTHER PUBLICATIONS

E. Bodio, "The Application of Multiple-Component Gaseous Mixtures in Linde-Hampson Type Refrigerators" Proceedings of the Institute of Thermal Technology and Fluid Mechanics, Wroclaw Polytechnic Institute, (Wroclaw Polytechnic Institute, 1985).

(Continued)

*Primary Examiner* — Melanie Hand
(74) *Attorney, Agent, or Firm* — Fish & Richardson P.C.

(57) ABSTRACT

A sheath for use with a cryoprobe in a cryosurgical procedure can have an opening at its proximal end configured to be inserted over a tip portion of a cryoprobe. The sheath can be connected to the cryoprobe with an end connector. Sheath can have a tip located at its distal that can have a trocar configuration for tissue penetration. A cylindrical section located inwardly from the tip can have a spiral groove defined on an exterior surface. At least one wire can be disposed within the groove so as to fit within the outer perimeter of the sheath. Wires disposed in grooves can include heating elements and temperature sensing elements. Sheath can further include a graduated catheter located inwardly from the cylindrical section and a handle located inwardly from the graduated catheter.

8 Claims, 4 Drawing Sheets

U.S. PATENT DOCUMENTS

| | | |
|---|---|---|
| 5,758,505 A | 6/1998 | Dobak, III et al. |
| 5,910,104 A | 6/1999 | Dobak, III et al. |
| 6,035,657 A | 3/2000 | Dobak, III et al. |
| 6,151,901 A | 11/2000 | Dobak, III et al. |
| 6,182,666 B1 | 2/2001 | Dobak, III |
| 6,193,644 B1 | 2/2001 | Dobak, III et al. |
| 6,237,355 B1 | 5/2001 | Li |
| 6,241,722 B1 | 6/2001 | Dobak et al. |
| 6,270,494 B1 | 8/2001 | Kovalcheck et al. |
| 6,306,129 B1 | 10/2001 | Little et al. |
| 6,451,012 B2 | 9/2002 | Dobak, III |
| 6,471,694 B1 | 10/2002 | Kudaravalli et al. |
| 6,475,212 B2 | 11/2002 | Dobak, III et al. |
| 6,530,234 B1 | 3/2003 | Dobak, III et al. |
| 6,878,204 B1 | 4/2005 | Kinnison et al. |
| 7,381,208 B2 | 6/2008 | Von der Walt et al. |
| 2007/0277550 A1 | 12/2007 | Li et al. |
| 2008/0027422 A1 | 1/2008 | Vancelette et al. |
| 2008/0114344 A1 | 5/2008 | Xiao et al. |
| 2008/0114347 A1 * | 5/2008 | Devens et al. .................. 606/23 |
| 2008/0119833 A1 | 5/2008 | Vancelette et al. |
| 2008/0119837 A1 | 5/2008 | Devens et al. |
| 2008/0119838 A1 | 5/2008 | Vancelette et al. |
| 2008/0119840 A1 | 5/2008 | Vancelette et al. |

FOREIGN PATENT DOCUMENTS

| | | |
|---|---|---|
| EP | 0655225 | 5/1995 |
| GB | 1336892 | 11/1973 |
| GB | 2094636 | 9/1982 |
| GB | 2226497 | 7/1990 |
| GB | 2244922 | 12/1991 |
| GB | 2283678 | 5/1995 |
| WO | 93/04647 | 3/1993 |
| WO | 95/13025 | 5/1995 |

OTHER PUBLICATIONS

Kobrianskiy et al., "A Cryomedical Device Based on a Closed-Cycle Joule-Thompson Cooling System," Nos. 8-9 Elektronnaya Promyyschlennost [Electronics Industry] at 71-71 (1979).

W.A. Little, "*Advances in Joule-Thompson Cooling,*" 35 Advances in Cryogenic Engineering 1305-1314 (1990) ("Little I").

W.A. Little, "*Microminiature Refrigeration,*" 55 (5) Rev. Sci. Instrum. at 661-680 (May 1984 ("Little II").

Coxeter, "Developments to Watch: The Deep Freeze for Irregular Heartbeats," *Business Week*, No. 3390, Sep. 19, 1994, p. 90.

Chang, Ph.D. et al., "Development of a High-Performance Multiprobe Cryosurgical Device", Biomedical Instrumentation & Technology, vol. 28, No. 5, Sep./Oct. 1994, pp. 383-390.

\* cited by examiner

DISPOSABLE SHEATH WITH REPLACEABLE CONSOLE PROBES FOR CRYOSURGERY

PRIORITY CLAIM

The present application claims priority to U.S. Provisional Application Ser. No. 60/866,335, filed Nov. 17, 2006 and entitled "DISPOSABLE SHEATH WITH REPLACEABLE CONSOLE PROBES FOR CRYOSURGERY", which is herein incorporated by reference in its entirety.

FIELD OF THE INVENTION

The present invention relates to cryoprobes for use in cryosurgical systems. More specifically, the present invention is directed to a disposable sheath for placement over a cryoprobe during cryosurgical procedures.

BACKGROUND OF THE INVENTION

Cryosurgical probes are used to treat a variety of diseases. Cryosurgical probes quickly freeze diseased body tissue, causing the tissue to die after which it will be absorbed by the body, expelled by the body, sloughed off or replaced by scar tissue. Cryothermal treatment can be used to treat prostate cancer and benign prostate disease. Cryosurgery also has gynecological applications. In addition, cryosurgery may be used for the treatment of a number of other diseases and conditions including breast cancer, liver cancer, glaucoma and other eye diseases.

A variety of cryosurgical instruments variously referred to as cryoprobes, cryosurgical probes, cryosurgical ablation devices, cryostats and cryocoolers have been used for cryosurgery. These devices typically use the principle of Joule-Thomson expansion to generate cooling. They take advantage of the fact that most fluids, when rapidly expanded, become extremely cold. In these devices, a high pressure gas mixture is expanded through a nozzle inside a small cylindrical shaft or sheath typically made of steel. The Joule-Thomson expansion cools the steel sheath to a cold temperature very rapidly. The cryosurgical probes then form ice balls which freeze diseased tissue without undue destruction of surrounding healthy tissue.

Cryosurgery often involves a cycle of treatments in which the targeted tissue is frozen, allowed to thaw and then refrozen. Double and even triple thaw cycles are now commonly performed. Comparison with single freeze thaw cycle shows that the second freeze will increase damage to the diseased tissue and thus the efficiency of the treatment.

A typical cryosurgical probe will include one or more auxiliary instruments near the cold tip. Such instruments include electrical heaters and temperature sensors. Frequently the cold tip must be interchangeable with various shapes, dimensions, and edges so as to perform different surgical procedures. Moreover, there is a need to that the probe be capable of sterilization for repeated surgical procedures. Thus there is a need for a disposable compact sheath with integrated capabilities for the auxiliary equipment, and a coupling system for facilitating probe end replacement when necessary.

SUMMARY OF THE INVENTION

The present invention is directed to a cryoprobe for use in cryosurgical systems. Cryoprobes for prostate cancer treatment frequently include an integrated electric heater and thermocouple for measuring temperature. The present invention is a cost effective and easy-to-operate sterile disposable cover or sheath for small diameter, non-sterile cryoprobe ends attached to a cryosurgical system. The present invention further provides a means for periodically replacing the system's cryoprobe ends.

In one aspect of the present invention, a hollow sheath is provided for cryoprobes, said sheath acting as a protective cover. The sheath generally includes a distal end with a trocar tip for tissue penetration and insertion into the area designated for treatment. In this aspect, the tip is shaped for prostate treatment. Inboard from the trocar tip is a cylindrical section that includes a spiral groove on the exterior surface. The groove may have a constant depth and width. The cylindrical section is generally proximate the treatment area. Heater elements and thermocouple or similar sensors, in a wire configuration, are disposed within the groove so as to fit within the outer margin of the sheath. The heater and thermocouple elements are fed into the groove at the inboard start of the groove.

Inboard of the heater/thermocouple section is a graduated catheter followed by a larger diameter probe handle. The graduated catheter has the same general diameter as the heater/thermocouple section. The graduated catheter includes an internal path for routing of the heater and thermocouple wires. A frustoconical transition section extends from the graduated cylinder to the probe handle. The probe handle may have a diameter greater than the diameter of the graduated cylinder. The probe handle may include an internal path for the heater and thermocouple wires.

The proximal end of the sheath includes an end connector. The geometry on the end of the sheath probe handle is sized to mate with the handle of the permanent probe handle. The end connector can include a nut and thread connection for fastening onto the permanent probe. Conversely the permanent probe can include a nut for mating with a threaded end connector of the sheath. The end connector can also comprise a twist-on nut, a button release, a compression fitting or the like.

The end connector can also include the mechanical and electrical connectors for attaching and removing the sheath from the cryoprobes. The mechanical connections can include fluid couplers to facilitate probe end replacement. The electrical connections can include terminal contacts for the electric heater and thermocouple. The terminals are operably connected to the heater and temperature sensor, respectively by internal wiring.

It is further envisioned that a plastic drape or sterile barrier is attached to the sheath. The drape can be sized and dimensioned so as to extend over the additional length of the permanent system's non-sterile probe lines thus completing the sterile coverage of the system.

In another aspect of the present invention insulated fluid couplers are disposed in the system's probe lines to facilitate probe end replacement when required. Internal valving operably connected to one or more pumps and tubing shuttle gas out of the probe lines for storage in an internal reservoir during probe end replacement. In addition the valve and pump system can be used to increase efficiency during non-operational times. The present invention may further include means to remove air from the system after probe replacement.

The above summary of the various representative embodiments of the invention is not intended to describe each illustrated embodiment or every implementation of the invention. Rather the embodiments are chosen and describe so that other skilled in the art may appreciate and understand the principles

BRIEF DESCRIPTION OF THE FIGURES

These as well as other objects and advantages of this invention, will be more completely understood and appreciated by referring to the following more detailed description of the presently preferred exemplary embodiments of the invention in conjunction with the accompanying drawings of which.

DETAILED DESCRIPTION

Figure 1:
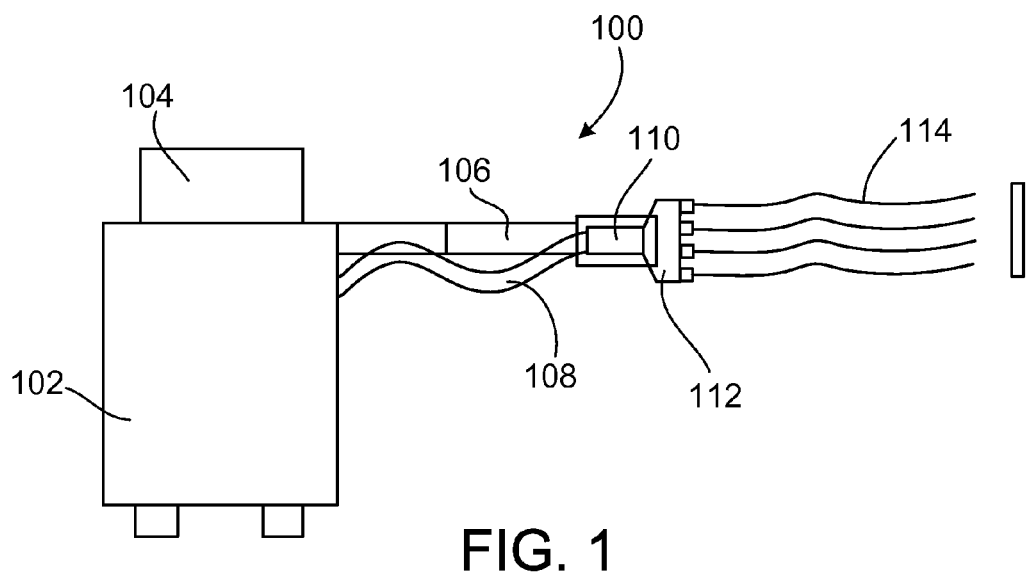
FIG. 1 is a schematic illustration of an embodiment of a cryosurgical system according to the present disclosure.

A closed loop cryosurgical system 100 according to the present disclosure is illustrated in FIG. 1. Cryosurgical system 100 can include a refrigeration and control console 102 with an attached display 104. Control console 102 can contain a primary compressor to provide a primary pressurized, mixed gas refrigerant to the system and a secondary compressor to provide a secondary pressurized, mixed gas refrigerant to the system. Control console 102 can also include controls that allow for the activation, deactivation, and modification of various system parameters, such as, for example, the flow rates, pressures, and temperatures of the refrigerants. Display 104 can provide the operator the ability to monitor, and in some embodiments adjust, the system to ensure it is performing properly and can provide real-time display as well as recording and historical displays of system parameters. One exemplary console that can be used with an embodiment of the present invention is used as part of the Her Option® Office Cryoablation Therapy available from American Medical Systems of Minnetonka, Minn.

The high pressure primary refrigerant is transferred from control console 102 to a cryostat heat exchanger module 110 through a flexible line 108. The cryostat heat exchanger module or cryostat 110 transfers the refrigerant into and receives refrigerant out of one or more cryoprobes 114. The particular cryoprobe configuration will depend on the application for which the system is used. For example, a uterine application will typically use a single, rigid cryoprobe, while a prostate application will use a plurality of flexible cryoprobes (which is shown in the embodiment of FIG. 1). If a single, rigid cryoprobe is used, the elements of the cryostat heat exchanger module 110 may be incorporated into a handle of the cryoprobe. If a plurality of flexible cryoprobes are used, a manifold 112 may be connected to cryostat heat exchanger module 110 to distribute the refrigerant among the several cryoprobes. The cryostat heat exchanger module 110 and cryoprobes 114 can also be connected to the control console 102 by way of an articulating arm 106, which may be manually or automatically used to position the cryostat heat exchanger module 110 and cryoprobes 114. Although depicted as having the flexible line 108 as a separate component from the articulating arm 106, cryosurgical system 100 can incorporate the flexible line 108 within the articulating arm 106.

Figure 2:
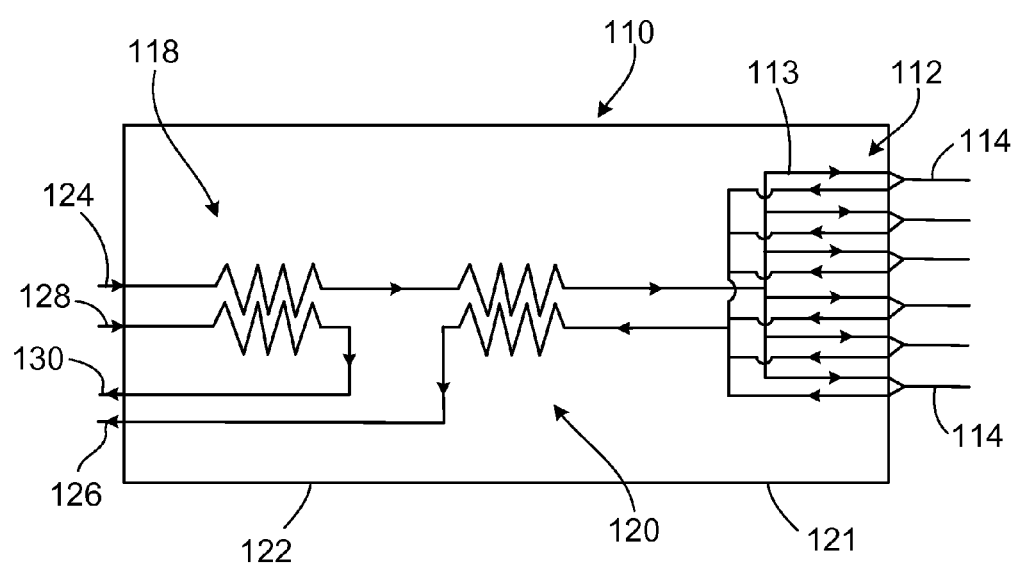
FIG. 2 is a side view of a cryostat heat exchanger module according to an embodiment of the present invention.

Referring now to FIG. 2, there can be seen an embodiment of a cryostat heat exchanger module 110 according to the present disclosure. The cryostat 110 may contain both a pre-cool heat exchanger, or pre-cooler 118, and a recuperative heat exchanger, or recuperator 120. A vacuum insulated jacket 122 surrounds the cryostat 110 to prevent ambient air from warming the refrigerant within the cryostat 110 and to prevent an outer surface 121 of the cryostat 110 from becoming excessively cold. High pressure primary refrigerant 124 enters the cryostat 110 and is cooled by high pressure secondary refrigerant 128 that is expanded to a lower temperature in the pre-cool heat exchanger 118. The resulting low pressure secondary refrigerant 130 then returns to the secondary compressor to be repressurized. Since the secondary refrigerant does not flow into the probes 114 (which are brought into direct contact with the patient), a higher pressure can be safely used for the secondary refrigerant 128, 130 than the primary refrigerant 124, 126.

The high pressure primary refrigerant 124 then continues into the recuperator 120 where it is further cooled by the low pressure primary refrigerant 126 returning from the manifold 112. The low pressure primary refrigerant 126 is colder than the high pressure primary refrigerant because it has undergone Joule-Thompson expansion in the plurality of probes 114. Recuperator 120 is preferably incorporated into the cryostat 110. Alternatively, tubing coils inside each probe 114 can act as recuperative heat exchangers in order to reduce insulation requirements and return low pressure primary refrigerant 126 to the console 102.

After leaving the recuperator 120, high pressure primary refrigerant 124 flows into the manifold 112, where it is distributed into multiple flexible probes 114. In one presently contemplated embodiment, six probes are connected to manifold 112, but one of skill in the art will recognize that greater or fewer probes may be used depending on the needs of a particular procedure. In each probe 114, the high pressure primary refrigerant 124 flows into a Joule-Thompson expansion element, such as a valve, orifice, or other type of flow constriction, located near the tip of each probe 114. At the expansion element, high pressure primary refrigerant 124 is expanded isenthalpically to further reduce its temperature. In one presently preferred embodiment, the Joule-Thompson expansion elements are capillary tubes. The expansion element converts high pressure primary refrigerant 124 into low pressure primary refrigerant 126 which cools a heat transfer element mounted in the wall of probe 114, allowing the probe 114 to form ice balls at the tip to freeze diseased tissue. The low pressure primary refrigerant 126 then exits the manifold 112, travels through the recuperator 120 (where it serves to further cool the high pressure primary refrigerant 124), flows past the precooler 118 and back to the primary compressor in the console 102, where it is compressed back into high pressure primary refrigerant 124 so that the above process is repeated.

Figure 3:
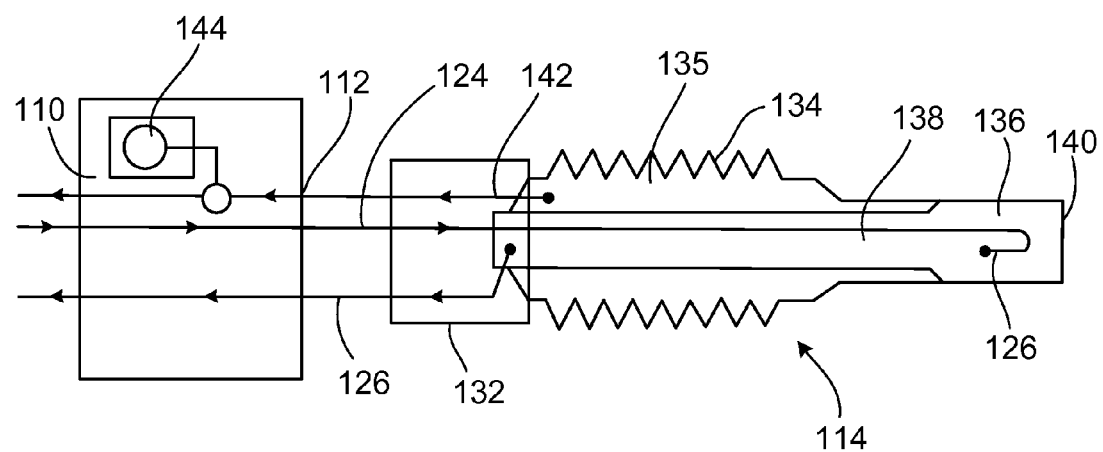
FIG. 3 is a schematic illustration of a vacuum insulated cryoprobe for use with the cryosurgical system of the present invention.

Referring now to FIG. 3, there can be seen an embodiment of a vacuum insulated flexible probe 114 according to the present disclosure. Probe 114 includes a quick-disconnect coupling 132 that mates with the manifold 112 to connect the probe 114 to the cryosurgical system 100. The quick-disconnect coupling 132 includes pathways for high pressure primary refrigerant 124 and low pressure primary refrigerant 126 to flow between the manifold 112 and the probe 114. Probe 114 also includes a flexible conduit 134 and a rigid probe end 138 contained partially therein. Flexible conduit 134 may incorporate feature such as, bellows, corrugated or convoluted portions or Nitinol tubing to increase flexibility. Flexible conduit 134 covers only a portion of rigid probe end 138, leaving freeze portion 136 exposed. Freeze portion 136 is preferably 30-40 mm long and a tip 140 of freeze portion 136 is preferably about 2.1 mm in diameter. Probe 114 further includes fluid pathways 124, 126 for high pressure primary refrigerant and low pressure primary refrigerant. Probe 114 also includes a Joule-Thompson expansion element to expand (and thereby further cool) the high pressure primary refrigerant 124.

As pictured in FIG. 3, quick-disconnect coupling 132 may be located at the proximal end of probe 114 at its connection with manifold 112. In this configuration, the entire probe 114 is disposable. Alternatively, the vacuum insulated flexible conduit 134 may be permanently attached to manifold 112, with the quick-disconnect coupling connected to the proximal end of the rigid probe end 138 such that only rigid probe end 138 is disposable.

To facilitate an efficient replacement of probe 114, insulated fluid couplers should be used. Furthermore, within cryostat heat exchanger module 110 or control console 102, a separate pump system should be established operably connected to the high pressure primary refrigerant 124, low pressure primary refrigerant 126, high pressure secondary refrigerant 128, and low pressure secondary refrigerant 130. The pump system would transfer fluid from the probe lines for storage in a reservoir during probe replacement and possibly during the non-operational times. A vacuum pump would also be operably connected to high pressure primary refrigerant 124, low pressure primary refrigerant 126, high pressure secondary refrigerant 128, and low pressure secondary refrigerant 130 for removing air that enters the system during replacement.

In order to actively evacuate an insulation space 135 within the flexible conduit 134, an additional insulation communication channel 142 through the quick-disconnect coupling 132 between the probe 114 and the cryostat 110 can be provided. Because of this, each time the quick-disconnect coupling 132 is connected to the cryostat 110, air will be introduced into the insulation space 135. Air can be evacuated from the insulation space 135, however, by one or more of a getter chamber 144 located within the cryostat, a vacuum pump located within the control console 102, or by activation of one of the console compressors to pull the gases out of the insulation space prior to introduction of refrigerant into the circuit. For example, prior to operation of the system a compressor in the console and/or other vacuum pumps may be used to evacuate gases not only from the insulation space 135 through the insulation communication channel 142, but also from the high pressure primary refrigerant 124 and low pressure primary refrigerant 126 channels. The probe 114 can then be connected to a pre-activated getter chamber 144 in the cryostat 110 held at a low pressure to maintain the required low vacuum in the insulation space 135 while the system is in operation.

Maintaining a vacuum within insulation space 135 surrounding portions of the probe serves multiple functions. It limits the freeze portion 136 which makes it easier to confine the freezing process to a small area of damaged tissue. It also helps maintain the low temperature of the low pressure primary refrigerant 126 as it returns to the cryostat. This allows the low pressure primary refrigerant 126 to better cool the high pressure primary refrigerant 124 in the recuperator 120. It also helps prevent unwanted frosting and low temperatures on the outer jacket of the flexible conduit 134. In addition, creating a vacuum within the insulation space 135 with control console 102 based pumping and/or getter evacuation also reduces the cost and complexity of manufacturing the probes 114. Alternatively, foam, aerogel, air, or noble gas gaps can also be used for insulation.

Figure 4:
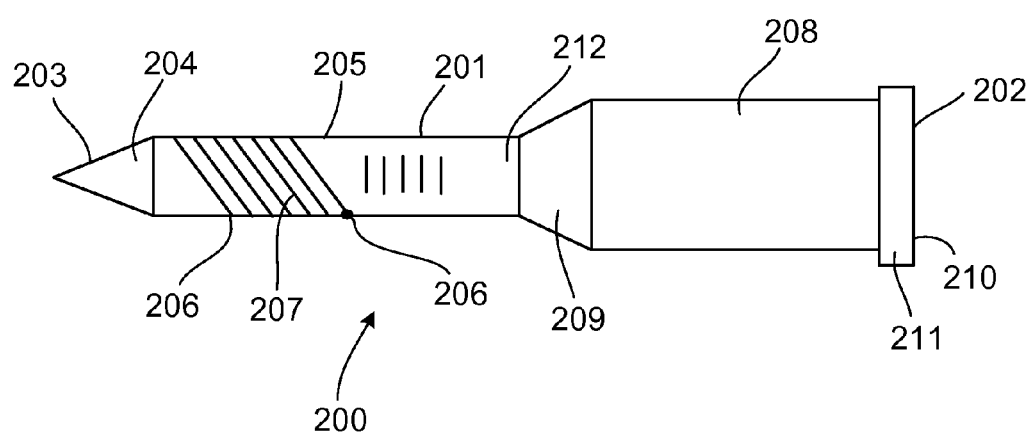
FIG. 4 is a side view of an embodiment of a cryoprobe sheath according to the present invention.

A representative cryoprobe 114 used with the previously discussed cryosurgical systems of the present disclosure can also include a protective, disposable sheath 200, as illustrated in FIG. 4. Sheath 200 includes a sheath body 201 that is positionable over cryoprobe 114 by inserting the cryoprobe tip portion 136 into a sheath opening 202. Sheath 200 is preferably constructed of a thermally resistive material, such as a rigid plastic. The sheath 200 generally includes a distal end 203 with a trocar tip 204 for tissue penetration and insertion into the area designated for treatment. In this aspect, the tip 204 is shaped for prostate treatment. Inboard from the trocar tip 204 is a cylindrical section 205 that includes a spiral groove 206 on the exterior surface. The groove 206 may have a constant depth and width. The cylindrical section 205 is generally proximate the treatment area. Thermal wires 207 in the form of resistive heater elements, thermocouple wires or similar sensors present in a wire configuration are disposed within the groove 205 so as to fit or otherwise reside within an outer margin or perimeter of the sheath 200. The thermal wires 207 can be fed into the groove 205 at the inboard start of the groove 205 at aperture 206.

In some representative embodiments, thermal wires 207 are evenly distributed around and/or through sheath 200. Thermal wires 207 can comprise a plurality of operably distinct wires or can comprise a single continuous wire wrapped about the sheath 200. Providing thermal power around the sheath 200 can reduce the time needed to thaw frozen tissue. Where multiple freeze-thaw cycles are employed, this can significantly reduce the time it takes to complete a cryosurgical procedure. Once a targeted area of tissue is frozen, the flow of refrigerant through cryoprobe(s) 114 is stopped using control console 102. Control console 102 is then used to power the thermal wires 207 so that they can be used to thaw the frozen tissue. Once the tissue is sufficiently thawed, thermal power is removed from the thermal wires 207.

Inboard of the cylindrical section 205 is a graduated catheter 212 followed by a larger diameter probe handle 208. The graduated catheter 212 has the same general diameter as the cylindrical section 205. The graduated catheter 212 includes an internal path for routing of the thermal wires 207. A frustoconical transition section 209 extends from the graduated catheter 212 to the probe handle 208. The probe handle 208 can have a diameter greater than the diameter of the graduated catheter 212. The probe handle 208 can include an internal path for the thermal wires 207.

The proximal end 210 of the sheath 200 includes an end connector 211. The geometry on the end of the sheath probe handle 208 is sized to mate with the handle of the permanent probe handle. The end connector 211 can comprise a nut and thread connection for fastening onto the permanent probe. Conversely the permanent probe can include a nut for mating with a threaded end connector 211 of the sheath 200. The end connector 211 can comprise a variety of suitable configurations such as, for example, a twist-on nut, a button release, a compression style fitting or other connectors suitable to the application.

The end connector 211 can also include the mechanical and electrical connectors for attaching and removing the sheath from the cryoprobes 114. The mechanical connections can include fluid couplers to facilitate probe end replacement. The electrical connections can include terminal contacts for the electric heater and thermocouple. The terminals are operably connected to the heater and temperature sensor, respectively by internal wiring.

Following completion of a cryosurgical procedure, end connector 211 can be disconnected such that cryoprobe 114 can be slidably withdrawn from the sheath opening 202. With the sheath 200 detached from the cryoprobe 114, the sheath 200 can be disposed of as conventional medical waste. In this manner, sheath 200 allows a medial professional to protect the more delicate construction of the cryoprobe 114 while maintaining sterile operating conditions by replacing used sheaths with new sheaths prior to commencing a cryosurgical procedure.

While the invention has been described in connection with what is presently considered to be the most practical and preferred embodiments, it will be apparent to those of ordinary skill in the art that the invention is not to be limited to the disclosed embodiments. It will be readily apparent to those of ordinary skill in the art that many modifications and equivalent arrangements can be made thereof without departing from the spirit and scope of the present disclosure, such scope to be accorded the broadest interpretation of the appended claims so as to encompass all equivalent structures and products.

The invention claimed is:

1. A protective sheath for use with a cryoprobe in a cryosurgical procedure, comprising:
   a sheath body having a proximal insertion end and a distal tip end, the proximal insertion end defining a sheath opening adapted to receive a tip portion of a cryoprobe, the proximal insertion end further including an end connector for retainably attaching the sheath body over the cryoprobe, wherein the sheath body further comprises a spiral groove proximate the distal tip end, the spiral groove including one or more thermal wires for selectively heating the distal tip end, and the spiral groove having a groove depth such the one or more thermal wires reside within a perimeter margin defined by the sheath body.

2. The protective sheath of claim 1, wherein the spiral groove further comprises a groove aperture at a proximal groove location, wherein the one or more thermal wires are fed through the groove aperture such that the one or more thermal wires are connectable to a power source through the sheath opening.

3. The protective sheath of claim 2, wherein the one or more thermal wires includes a temperature sensing element and a heater wire.

4. A protective sheath for use with a cryoprobe in a cryosurgical procedure, comprising:
   a sheath body having a proximal insertion end and a distal tip end, the proximal insertion end defining a sheath opening adapted to receive a tip portion of a cryoprobe, the proximal insertion end further including an end connector for retainably attaching the sheath body over the cryoprobe, wherein the distal tip end comprises a trocar configuration.

5. A protective sheath for use with a cryoprobe in a cryosurgical procedure, comprising:
   a sheath body having a proximal insertion end and a distal tip end, the proximal insertion end defining a sheath opening adapted to receive a tip portion of a cryoprobe, the proximal insertion end further including an end connector for retainably attaching the sheath body over the cryoprobe, wherein the end connector is selected from the group consisting of a threaded connector, a compression fitting and a spring-biased member.

6. A method of performing a cryosurgical procedure, comprising:
   providing a disposable sheath having a proximal insertion end and a distal tip end;
   inserting a cryoprobe into a sheath opening at the proximal insertion end;
   supplying a refrigerant to the cryoprobe to freeze tissue at the distal tip end;
   stopping the flow of refrigerant through the cryoprobe;
   powering at least one heating wire on the sheath body to heat the distal tip end;
   thawing frozen tissue with the heated distal tip end;
   removing the disposable sheath from the cryoprobe; and
   discarding the disposable sheath.

7. The method of claim 6, further comprising:
   insulating a proximal portion of the cryoprobe to define a freeze portion at a cryoprobe tip.

8. A method of performing a cryosurgical procedure, comprising:
   providing a disposable sheath having a proximal insertion end and a distal tip end;
   inserting a cryoprobe into a sheath opening at the proximal insertion end;
   supplying a refrigerant to the cryoprobe to freeze tissue at the distal tip end; and
   insulating a proximal portion of the cryoprobe to define a freeze portion at a cryoprobe tip, wherein insulating the proximal portion includes maintaining a vacuum within an insulation spaced defined at the proximal portion of the cryoprobe.

* * * * *